(12) United States Patent
Cohen et al.

(10) Patent No.: US 10,815,507 B2
(45) Date of Patent: Oct. 27, 2020

(54) METHOD FOR COMBINED PREPARATION OF BIODIESEL

(71) Applicant: TECHNION RESEARCH & DEVELOPMENT FOUNDATION LIMITED, Haifa (IL)

(72) Inventors: Yachin Cohen, Haifa (IL); Dmitry M. Rein, Nesher (IL); Lev Vaikhanski, Nesher (IL); Gilad Alfassi, Kiryat Motzkin (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 62 days.

(21) Appl. No.: 15/758,027

(22) PCT Filed: Sep. 7, 2016

(86) PCT No.: PCT/IL2016/050988
§ 371 (c)(1),
(2) Date: Mar. 7, 2018

(87) PCT Pub. No.: WO2017/042804
PCT Pub. Date: Mar. 16, 2017

(65) Prior Publication Data
US 2018/0251799 A1 Sep. 6, 2018

(30) Foreign Application Priority Data
Sep. 7, 2015 (IL) .......................... 241268

(51) Int. Cl.
| | |
|---|---|
| *C12P 7/64* | (2006.01) |
| *C12P 7/16* | (2006.01) |
| *C12P 19/14* | (2006.01) |
| *C12N 1/22* | (2006.01) |
| *C08H 8/00* | (2010.01) |
| *C12P 7/10* | (2006.01) |
| *C12N 9/20* | (2006.01) |
| *C12N 9/26* | (2006.01) |

(52) U.S. Cl.
CPC ................ *C12P 7/649* (2013.01); *C08H 8/00* (2013.01); *C12N 1/22* (2013.01); *C12P 7/10* (2013.01); *C12P 7/16* (2013.01); *C12P 19/14* (2013.01); *C12N 9/20* (2013.01); *C12N 9/2411* (2013.01); *C12Y 302/01001* (2013.01); *C12Y 302/01002* (2013.01); *C12Y 302/01003* (2013.01); *C12Y 302/01041* (2013.01); *Y02E 50/10* (2013.01); *Y02E 50/13* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2009/0117635 A1* 5/2009 Bradley ................ C12N 9/242
435/165
2015/0155068 A1 6/2015 Rein et al.

FOREIGN PATENT DOCUMENTS

| BE | 422877 A | 8/1937 |
|---|---|---|
| WO | 2013175379 A2 | 11/2013 |

OTHER PUBLICATIONS

Kuo et al. Bioresour Technol. Sep. 2015;192:54-9. Epub May 19, 2015. (Year: 2015).*
Harris et al. Curr Opin Chem Biol. Apr. 2014;19:162-70 (Year: 2014).*
Zhu et al. Biosci Biotechnol Biochem. 2012;76(4):671-8 (Year: 2012).*
Dmitry M. Rein et al: "Cellulose as a novel amphiphilic coating for oil-in-water and water-in-oil dispersions", Journal of Colloid and Interface Science, vol. 86, No. 1, Nov. 15, 2012, pp. 456-463.
International Search Report PCT/IL2016/050988 completed Nov. 23, 2016; dated Nov. 27, 2016 9 pages.
Written Opinion of the International Searching Authority PCT/IL2016/050988 dated Nov. 27, 2016 5 pages.

* cited by examiner

*Primary Examiner* — Christian L Fronda
(74) *Attorney, Agent, or Firm* — The Roy Gross Law Firm, LLC; Roy Gross (57) ABSTRACT

The present invention provides, inter alia, a method for combined preparation of saccharides, alcohols (biofuel) and biodiesel using a composition comprising interior hydrophobic or hydrophilic medium encapsulated by a layer comprising cellulose, cellulose derivative material, and/or starch surrounded by a hydrophilic or hydrophobic medium, respectively.

18 Claims, 3 Drawing Sheets

METHOD FOR COMBINED PREPARATION OF BIODIESEL

RELATED APPLICATIONS

This application is a National Phase of PCT Patent Application No. PCT/IL2016/050988 having International filing date of Sep. 7, 2016, which claims the benefit of priority from Israel Patent Application No. 241268, filed on Sep. 7, 2015. The content of the above documents are incorporated by reference in their entirety as if fully set forth herein.

FIELD OF INVENTION

The present invention relates, in some embodiments thereof, to a method for combined preparation of saccharides, alcohols and biodiesel using a composition comprising interior hydrophobic or hydrophilic medium encapsulated by a layer comprising cellulosic material and/or starch surrounded by a hydrophilic or hydrophobic medium, respectively.

BACKGROUND OF THE INVENTION

Encapsulation is a process in which tiny particles or droplets are surrounded by a coating to impart many useful properties to small capsules. In a relatively simplistic form, a microcapsule is a small sphere with a uniform wall around it. The material inside the microcapsule is referred to as the core, internal phase, or fill, whereas the wall is sometimes called a shell, coating, or membrane. Most microcapsules have diameters between a few tens of nanometers to a few millimeters. The core may be a crystal, a jagged adsorbent particle, an emulsion, a suspension of solids, or a suspension of smaller microcapsules. The microcapsule even may have multiple walls. The reasons for microencapsulation are countless. In some cases, the core must be isolated from its surroundings, as in isolating vitamins from the deteriorating effects of oxygen, retarding evaporation of a volatile core, improving the handling properties of a sticky material, or isolating a reactive core from chemical attack. In other cases, the objective is not to isolate the core completely but to control the rate at which it leaves the microcapsule, as in the controlled release of drugs or pesticides. The problem may be as simple as masking the taste or odor of the core, or as complex as increasing the selectivity of an adsorption or extraction process.

The technique of microencapsulation depends on the physical and chemical properties of the material to be encapsulated: complex coacervation, centrifugal extrusion, vibrational nozzle, spray-drying, interfacial polycondensation, interfacial cross-linking, in-situ polymerization, etc.

Non-food cellulosic biomass is the most abundant renewable bioresource as a collectable, transportable, and storable chemical energy that is far from fully utilized now. The production of biofuels and value-added biochemicals from evenly distributed non-food cellulosic biomass would decrease net greenhouse gas emissions by replacing the use of fossil fuels and would bring benefits to rural economy, national energy security, and the balance of trade.

The cost-effective release from cellulosic biomass of fermentable sugars for biorefineries has been a technical and economic issue. Saccharification of cellulosic biomass usually involves two sequential steps: (a) pretreatment (steam explosion, soaking in aqueous ammonia, concentrated acids or ionic liquids) which increases substrate reactivity for hydrolysis; and (b) hydrolysis, which releases soluble sugars using hot water treatment, acids or hydrolytic enzyme systems.

Biological enzymatic hydrolysis performances of various cellulolytic systems from individual cellulases, non-complexed cellulase mixtures, complexed cellulases (cellulosomes), and cell-surface cellulosomes are strongly associated with substrate reactivity of pretreated biomass.

The root causes of cellulose recalcitrance are attributed to a number of factors, such as: cellulose substrate chemical reagents accessibility, degree of polymerization, crystallinity, particle size and substrate porosity (intrinsic surface area). For enzymatic hydrolysis, the cellulose substrate enzymatic accessibility has shown to be the most important material characteristic, impacting efficient enzymatic cellulose hydrolysis at low enzyme loadings. This is due to the following causes: (a) enzymatic cellulose hydrolysis occurs only on the surface of hydrated cellulose molecules in the aqueous phase (b) for effective hydrolysis, enzymes must preferentially adsorb on the hydrophobic face of cellulose crystals or onto hydrophobic glucan planes of cellulose molecules.

Standard methods for partially overcoming cellulose recalcitrance to hydrolytic enzymes are steam explosion [Bura R, et al., *Appl. Biochem. Biotechnol.* 98/100, 59 (2002)], soaking in aqueous ammonia [Kim T H and Lee Y Y, *Bioresource Technol.* 97, 224 (2006)], concentrated acid [Pereira A N, et al. *Methods Enzymol.* 160, 26 (1988)] or ionic liquid pretreatment [Zhao H, et al. *J. Biotechnol.* 139, 47 (2009)].

US Application number 20150155068 of Rein and Cohen discloses composition having an interior hydrophobic space encapsulated by at least one non-derivatized cellulose molecular layer surrounded by a hydrophilic medium. This application further discloses methods for making an oil-in-water dispersion or water-in-oil dispersion by mixing a hydrophilic medium, a hydrophobic composition and non-derivatized cellulose solution in an ionic liquid or pure non-derivatized cellulose hydrogel.

SUMMARY OF THE INVENTION

The present invention relates, in some embodiments thereof, to a method for combined preparation of saccharides, alcohols (biofuels) and alcohols (e.g., alkyl alcohols) esterified oils (biodiesels), using a composition comprising interior hydrophobic or hydrophilic medium encapsulated by a layer comprising cellulosic material and/or starch surrounded by a hydrophilic or hydrophobic medium, respectively.

In one embodiment, the present invention provides a process for the preparation of biodiesel, comprising the steps of:

hydrolyzing a composition, wherein the composition comprises an interior hydrophobic or hydrophilic medium encapsulated by at least one layer, wherein the at least one layer:

(i) comprises at least one of cellulose, a cellulose derivative material, and starch; and (ii) is surrounded by a hydrophilic or hydrophobic medium, respectively, thereby forming saccharide compounds;

fermenting the saccharide compounds, thereby forming at least one alcoholic compound; and allowing the alcoholic compound to react with the hydrophobic medium, thereby forming a biodiesel.

In a further embodiment, the step of hydrolyzing and the step of fermenting the saccharide are performed simultaneously (e.g., in one-pot).

In a further embodiment, the step of fermenting the saccharide and the step of allowing the alcoholic compound to react with the hydrophobic medium are performed simultaneously (e.g., in one-pot).

In a further embodiment, the step of hydrolyzing, the step of fermenting the saccharide, and the step of allowing the alcoholic compound to react with the hydrophobic medium are performed simultaneously (e.g., in one-pot).

In a further embodiment, any other combination of the above-mentioned steps is performed simultaneously (e.g., in one-pot).

In a further embodiment, the composition comprises at least one layer of secondary cellulose acetate.

In a further embodiment, the composition is dispersed and/or emulsified.

In a further embodiment, the cellulosic material and/or the starch is nano sized. In a further embodiment the cellulose, the cellulose derivative material, and/or the starch is micro-sized.

In a further embodiment, the cellulose, the cellulose derivative material, and/or starch in form selected from hydrogel, amorphized structure, crystalline structure or mixture thereof.

In a further embodiment, the alcoholic compound selected from methanol and ethanol.

In a further embodiment, the layer is in a form selected from one or more continuous molecular layers, one or more groups of separated particles, and any mixture thereof.

In a further embodiment, the steps of emulsifying, hydrolyzing, fermenting, and allowing the alcoholic compound to react with the oil medium are performed sequentially.

In a further embodiment, the steps of emulsifying, hydrolyzing are performed simultaneously.

In a further embodiment, the steps of hydrolyzing and fermenting are performed simultaneously.

In a further embodiment, the steps of hydrolyzing, fermenting and allowing the alcoholic compound to react with the oil medium are performed simultaneously.

In a further embodiment, the step of fermenting and the step of allowing the alcoholic compound to react with the oil medium are performed simultaneously.

In a further embodiment, the steps of step hydrolyzing, fermenting, and allowing the alcoholic compound to react with the oil medium are performed simultaneously.

In a further embodiment, the steps emulsifying, hydrolyzing, fermenting, and allowing the alcoholic compound to react with the oil medium are performed simultaneously.

In a further embodiment, the disclosed steps are performed simultaneously. In a further embodiment, at least two of the disclosed steps are performed sequentially. In a further embodiment, at least two of the disclosed steps are performed simultaneously. In a further embodiment, at least two of the disclosed steps are performed sequentially and at least two of the disclosed steps are performed simultaneously.

In a further embodiment, two or more steps of the disclosed steps are performed in one-pot.

In a further embodiment, at least one alcoholic compound is maintained at an optimal concentration. In a further embodiment, the concentration ranges from 0.1% to 10% (v/v.). In a further embodiment, at least one alcoholic compound is maintained at a concentration that varies within ±30%.

In a further embodiment, the emulsified composition is selected from oil-in-water (o/w), water-in-oil (w/o) and any combination thereof.

In a further embodiment, the emulsified composition is devoid of a surfactant.

In a further embodiment, oil medium comprises one or more compounds selected from the group consisting of: natural vegetable, algae or organic oils (lipids), polyglycol, an alkane, an alkene, an alkyne, an aromatic hydrocarbon, or any combination thereof.

In a further embodiment, the composition is in a form of a capsule comprising a shell and a core.

In a further embodiment, the capsule is 10 nm to 1000 μm in diameter.

In a further embodiment, a thickness of the shell thickness ranges from about 0.1% to about 500% of the core.

In a further embodiment, cellulosic material is an emulsifying agent.

In a further embodiment, the emulsified composition comprises a cellulose hydrolyzing enzyme.

In a further embodiment, hydrolyzing enzyme is selected from the group consisting of α-amylase, β-amylase, isoamylase, glucoamylase, pullulanase, cyclodextrin glucano-transferase, β-fructofuranosidase, glucose isomerase, glycoside hydrolase and combinations thereof.

In a further embodiment, the biodiesel is a product of reaction of the alcoholic compound, with the interior hydrophobic medium.

In a further embodiment, the reaction of the alcoholic compound, with the oil medium is a transesterification step assisted by a catalyst.

In a further embodiment, the catalyst is selected from the group consisting of alkali-catalyst.

In a further embodiment, the catalyst is an enzyme selected lipases.

In a further embodiment, lipases are selected from *Ryzopus oryzae, Rhizomucor miehei, Mucor miehei, Pseudomonas fluorescens, Mucor javanicus, Candida rugosa* and *Rhizopus niveus,* as well as lipase OF from *Candida cylindracea* (*C. rugosa*) and lipase QLC from *Alcaligenes* sp. and a combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

The present invention, in some embodiments thereof, relates to a process for combined preparation of saccharide compounds, alcohols and/or biodiesel.

In some embodiments, the present invention relates to a process for combined preparation of saccharides, alcohols and biodiesel using a composition comprising interior hydrophobic or hydrophilic medium encapsulated by a layer comprising cellulosic material and/or starch, surrounded by a hydrophilic or hydrophobic medium, respectively.

In some embodiments, the process for the combined preparation of biodiesel comprises the steps of (a) hydrolyzing a composition comprising a cellulosic material and/or starch, thereby forming saccharide compounds; (b) fermenting the saccharide compounds, thereby forming at least one alcoholic compound (biofuel), and (c) allowing the alcoholic compound to react with an oil medium, thereby forming a biodiesel. In some embodiments, at least one of: steps (a) and (b); steps (b) and (c), and steps (a) to (c) is performed simultaneously, e.g., in one-pot. In some embodiments, the term "cellulosic material" refers to derivatized cellulose, e.g., cellulose acetate as defined hereinbelow.

In some embodiments, the process comprises the steps of emulsifying a composition comprising interior hydrophobic medium encapsulated by at least one layer; hydrolyzing the emulsified composition, thereby forming saccharide compounds; fermenting the saccharide compounds, thereby forming one or more alcoholic compounds (also referred to herein as: "biofuel" or alcohol); and allowing the alcoholic compound to react with the oil medium, thereby forming a biodiesel.

In some embodiments, the layer is a continuous molecular layer. In some embodiments, the layer comprises or is in the form of a group of particles. In some embodiments, the layer comprises or is in the form of a combination of a continuous molecular layer and a group of particles. The term "layer" may refer to one or more layers.

The term "continuous layer" is intended principally to cover the situation when adjacent cellulose molecules or cellulose particles and/or cellulose hydrogel droplets relics spread out and join together to form a thin uninterrupted layer but is not intended to exclude either layers with occasional voids or layers. The particles may be connected or separated.

In some embodiments, the process comprises the steps of emulsifying a composition comprising interior hydrophobic (oil) medium encapsulated by at least one layer; allowing the oil medium to react with alcoholic compound, wherein the alcoholic compound is added to the emulsified composition reaction medium, thereby forming a biodiesel. In some embodiments the alcoholic compound is added to an area surrounding the emulsified composition reaction medium.

In some embodiments, the process comprises the steps of hydrolyzing a remaining exhaust encapsulation cellulose layers, thereby forming saccharide compounds. In some embodiments, the biofuel (e.g., alcoholic compound) is returned to the emulsified composition reaction medium and reacts with oil medium thereby forming a biodiesel.

In some embodiments, the present invention provides the process for a preparation of saccharides comprising the steps of emulsifying a composition comprising interior hydrophobic medium (oil) encapsulated by one or more layers, thereby forming an emulsion; and hydrolyzing the emulsified composition, thereby forming saccharide compounds.

In some embodiments, the encapsulating layer comprises cellulosic material and/or starch particles surrounding a hydrophilic or hydrophobic medium. In some embodiments, the encapsulating layer comprising cellulosic material and/or starch particles is surrounded by a hydrophilic or hydrophobic medium. In some embodiments, the particles are in the form of hydrogel.

In some embodiments, the process comprises a step of emulsifying a composition comprising interior hydrophobic or hydrophilic medium encapsulated by layer(s), wherein the layer(s):

(i) comprise(s) a cellulosic material and/or starch; and
(ii) is/are surrounded by a hydrophilic or hydrophobic medium, respectively, thereby forming an emulsion;

Herein, the term "respectively" means that hydrophilic interior medium is surrounded by hydrophobic medium, or, alternatively, hydrophobic interior medium is surrounded by hydrophilic medium.

In some embodiments, the hydrophobic medium comprises one or more oils.

In some embodiments, the hydrophobic medium comprises one or more compounds selected or produced from, without being limited thereto, natural vegetable, algae, fish oils, Canola, coconut oil, castor oil, animal fat, rapeseed, soybeans, or organic oils (lipids), polyglycol, an alkane, an alkene, an alkyne, an aromatic hydrocarbon, or any combination thereof.

In some embodiments, prior to forming the emulsion the cellulose and/or starch containing raw material are blended with a solvent so as to dissolve the cellulose and/or starch.

In exemplary embodiments, the solvent(s) are selected from ionic liquids, urea/NaOH mixtures, phosphoric acid. In exemplary embodiments, the solvent(s) are selected from any solvent known in the art.

In some embodiments, the composition consists or comprises an interior hydrophobic space encapsulated by at least one cellulose molecular layer, wherein the cellulose is surrounded by a hydrophilic medium In some embodiments, the composition consists or comprises an interior hydrophilic space encapsulated by cellulose molecular layer, wherein the cellulose is surrounded by a hydrophobic medium. The terms "hydrophobic medium", "oil medium", or "oil" are used hereinthroughout interchangeably.

In some embodiments, the composition consists or comprises capsules in a hydrophilic medium, wherein the capsules having an interior hydrophobic space are separated from the hydrophilic medium by one or more layers consisting cellulose or starch.

In some embodiments, the composition consists or comprises capsules in a hydrophobic medium, wherein the capsules have an interior hydrophobic space separated from the hydrophobic medium by at least one layer consisting cellulose. In some embodiments, the composition described herein is devoid of a surfactant. In some embodiments, the composition described herein is oil-in-water composition. In some embodiments, the composition described herein is water-in-oil composition.

In some embodiments, the cellulosic material is, or is capable of being, in the form of hydrogel.

The term "hydrogel" as used herein refers to a network of natural or synthetic polymer chains capable to contain water.

The terms "cellulosic material" and "cellulosic bio mass" are used interchangeably and refer to materials that contain cellulose, in particular materials derived from plant sources that contain cellulose. Cellulose is a linear polysaccharide polymer composed of β-1,4 linked D-glucose molecules. It is the major component of plant cell walls.

In some embodiments, the cellulosic material is purified cellulose. In some embodiments, the cellulosic material is microcrystalline cellulose. As used herein, "microcrystalline cellulose" refers to purified, partially depolymerized cellulose prepared by treating alpha cellulose. Non-limiting examples of microcrystalline cellulose include microcrystalline cellulose sold under the trade name Avicel.®

In some embodiments, the cellulosic material is non-derivatized cellulose.

In some embodiments, the cellulosic material the cellulose is derivatized cellulose.

The term "derivatized cellulose" may denote a product in which hydroxyl groups of a cellulose product are partially or fully reacted with various reagents to afford derivatives. Cellulose esters and cellulose ethers are further non-limiting examples for such materials. More particularly, cellulose derivatives include ethyl cellulose, methyl cellulose, cellulose acetates e.g., secondary cellulose acetates (partially acetylated cellulose), cellulose triacetate, hydroxyalkylated cellulose, e.g., hydroxypropyl cellulose, carboxymethyl cellulose, hydroxypropylmethyl cellulose, hydroxyethyl methyl cellulose, etc.

In some embodiments, the cellulose acetate is in a degree of substitution in the range of about 0.3 to 1.5, e.g., 0.3, 0.4, 0.5, 0.6, 0.7, 0.8, 0.9, 1.0, 1.1, 1.2, 1.3, 1.4, or 1.5 including any value and range therebetween.

In other embodiments, the cellulosic material is a complex cellulosic material, which comprises cellulose and additional one or more complex polysaccharides or other polymers, typically polysaccharides and polymers of plant cell walls, such as hemicellulose and lignin.

As used herein, the term "hemicellulose" has its art-known meaning and refers to a group of branched polysaccharide hetero- or homo-polymers composed of a variety of sugar monomers. Hemicellulose includes, for example, and without being limited thereto, xylan, glucuronoxylan, arabinoxylan, glucomannan, and xyloglucan, in complex branched structures with a spectrum of substituents.

As used herein, the term "lignin" has its art-known meaning and refers to a polymeric material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

In some embodiments, the cellulosic material comprises cellulose, hemicellulose, and lignin. A cellulosic material containing cellulose, hemicellulose and lignin may be referred to as a "ligno-cellulosic material". In some embodiments, the cellulosic material is ligno-cellulosic.

The cellulosic material may include natural plant biomass and also paper waste and the like. Examples of suitable cellulosic materials include, but are not limited to, wheat straw, switchgrass, corn cob, corn stover, sorghum straw, cotton straw, bagasse, energy cane, hard wood paper, soft wood paper, algae, and combinations thereof. Each possibility represents a separate embodiment of the invention.

In some embodiments, the cellulosic material is crystalline.

The term "crystalline" as used herein, refers to a structure having three dimensional ordered arrangement of atoms or molecules, which possesses symmetry characteristics.

In some embodiments, the cellulosic material is amorphous.

The term "amorphous" as used herein refers to the lack of regular internally ordered arrangement, or the antithetical form of the crystalline form.

The terms "nano", "nanoscale" or "nano-sized" all refer to a range of from about 1 nanometer to about 1000 nanometers. A "nanoscale" therefore describes a scale in the above cited range and "nano-sized" describe particles and/or a composition or a formulation containing the particles, whereby the particles size is within the above cited range.

The terms "micro", "microscale" or "micro-sized" (also referred to herein interchangeably as "micron", "micronscale" or "micron-sized", respectively) all refer to a range of from about 1 micron to about 1000 microns. A "microscale" therefore describes a scale in the above cited range and "micro-sized" describes particles and/or a composition or a formulation containing the particles, where the particles size is within the above cited range.

In some embodiments, at least 80% of the capsules are characterized by a diameter that ranges from e.g., 10 nm to 1000 μm, or 10 nm to 100 nm, or 50 nm to 1 μm, or 100 nm to 100 μm, or 100 μm to 1000 μm. The term "diameter", as referred to herein, may refer to measurement of a longest dimension of a particle. The term "diameter" does not suggest that the particle is necessarily a sphere; most powder particles usually have random three-dimensional shapes.

In some embodiments, the capsule has a core-shell structure. In some embodiments, the shell thickness has a size that ranges from about 0.1% to about 500% of their inner (core) part. In some embodiments, the shell thickness has a size that ranges from about 1% to about 500% of their core part. In some embodiments, the shell thickness has a size that ranges from about 0.1% to about 100% of their core part. In some embodiments, the shell thickness has a size that ranges from about 0.5% to about 400% of their core part. In some embodiments, the shell thickness has a size that ranges from about 1% to about 300% of their core part. In some embodiments, the shell thickness has a size that ranges from about 10% to about 200% of their core part. In some embodiments, the shell thickness has a size that ranges from about 50% to about 300% of their core part.

Figure 1:
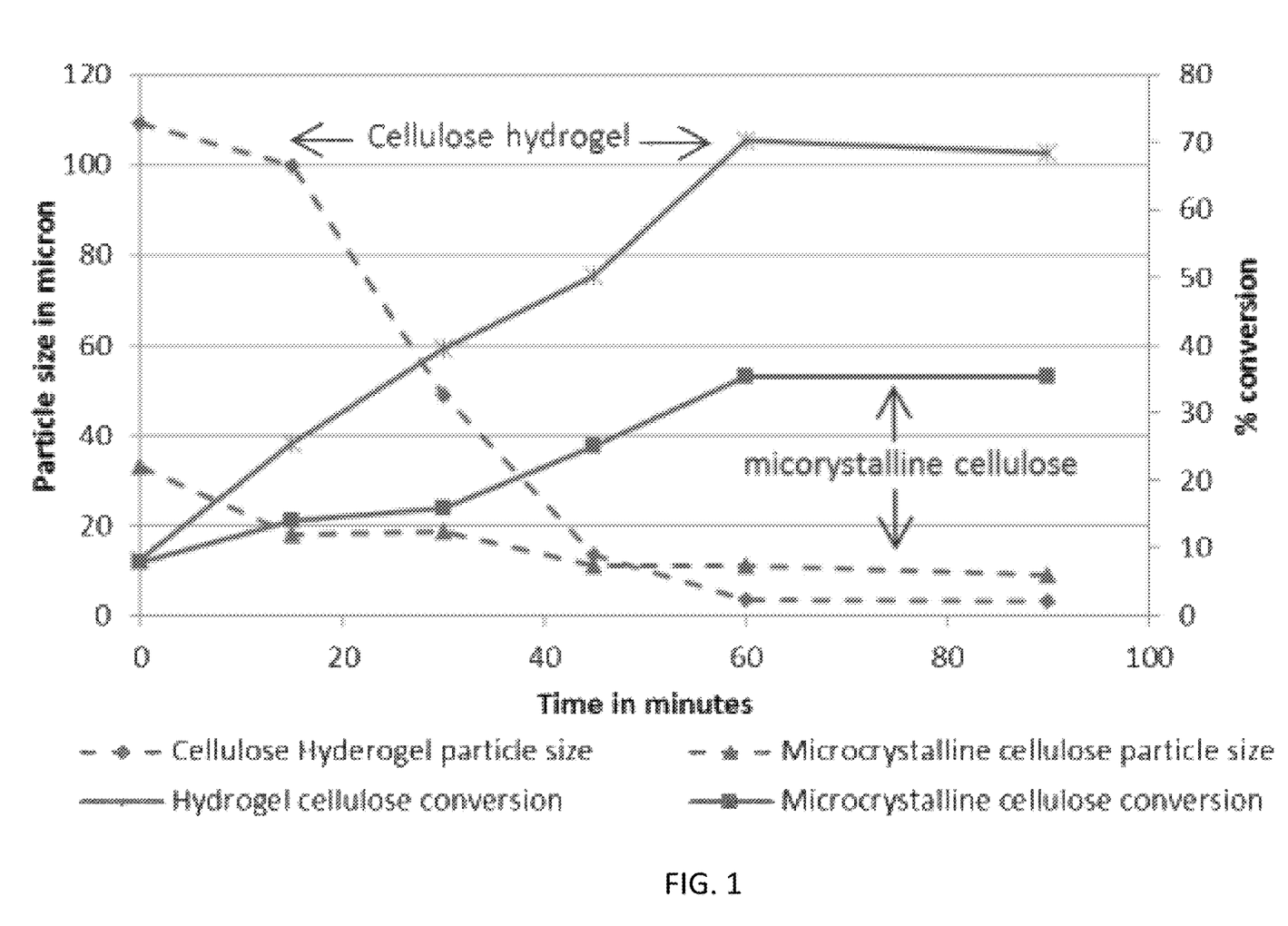
FIG. 1 presents graphs showing the enzymatic effect on the particle sizes and on glucose formation for cellulose hydrogel vs. microcrystalline cellulose.

Reference is now made to FIG. 1, which shows that as the hydrolyzing step proceeds, the cellulosic particles become smaller.

In some embodiments, cellulose in its unmodified form is utilized as an emulsifier for formation oil-in-water or water-in-oil dispersions based on encapsulation. In some embodiments, cellulose in its unmodified form is underivatized cellulose. In some embodiments, dried dispersions of hydrophobic compounds encapsulated by cellulose are readily regenerated by re-dissolution in water. In some embodiments, blowing of damp dispersions yields nanoporous cellulose foam (aerocellulose). In some embodiments, cellulose-encapsulated eicosane dispersions in solid or liquid form possess high effective heat-absorption capacity. In some embodiments, the encapsulating cellulose shell promotes the emergence of an irregular crystalline structure of the core material.

The term "hydrophilic", in some embodiments, refers to molecules that typically have polar groups. The term "hydrophobic", in some embodiments, refers to molecules that are typically free of polar groups. In some embodiments, the boundary between hydrophobicity and hydrophilicity occurs when the difference between the apolar attraction and the polar repulsion between molecules or particles of material immersed in water is equal to the cohesive polar attraction between the water molecules. Under these conditions, the interfacial free energy of interaction between particles of a material, immersed in water (ignoring electrostatic interactions), $\Delta G^{IF}$, is exactly zero. When the $\Delta G^{IF}$ is positive, the interaction of the material with water dominates and the surface of the material is hydrophilic; when $\Delta G^{IF}$ is negative, the polar cohesive attraction between the water molecules dominates and the material is hydrophobic. Thus, the sign of $\Delta G^{IF}$ defines the nature of the surface and the magnitude of $\Delta G^{IF}$ and is used, in some embodiments, as the natural quantitative measure of the surface hydrophobicity or hydrophilicity.

In some embodiments of the invention, cellulose molecules are ordered in the boundaries of the hydrophobic medium or space and water. Without being bound by any particular theory, it is assumed that the stabilization of the oil/water emulsion is affected by the presence of cellulose molecules in the boundaries of oil/water.

In some embodiments, an interior hydrophobic space is the core or the nucleus of a capsule of the invention which comprises a hydrophobic material such as, but not limited to, hydrocarbon. In some embodiments, an interior hydrophobic space comprises the hydrophobic interacting groups of underivatized cellulose.

In some embodiments, underivatized cellulose comprises up to 40% impurities. In some embodiments, underivatized cellulose comprises up to 35% impurities. In some embodiments, underivatized cellulose comprises up to 30% impurities. In some embodiments, underivatized cellulose comprises up to 25% impurities. In some embodiments, underivatized cellulose comprises up to 20% impurities. In some embodiments, impurities are organic impurities. In some embodiments, impurities include: lignin, hemicellulose, etc.

In some embodiments, an interior hydrophilic space is the core or the nucleus of a capsule of the invention which comprises a hydrophilic material such as, but not limited to, an aqueous solution. In some embodiments, an interior hydrophilic space comprises the hydrophilic interacting groups of underivatized cellulose.

In some embodiments, the medium is the solution which surrounds a capsule of the invention. In some embodiments, the medium is the solution which interacts with the outer surface of a capsule of the invention.

The term "emulsion" used herein to denote a system having at least two liquid phases, one of which is dispersed in the other. The dispersed phase is also referred to as inner phase, discontinuous phase, incoherent phase (the dispersed droplets) while the outer phase may also be referred to as coherent or continuous phase. Emulsions may comprise more than two phases. For example, emulsions may comprise of three liquid phases (i.e. triple emulsions), or two liquid phases and a solid phase. Common to all emulsions is that their outer phase is in a liquid state. If a third phase is present, such as a liquid or solid phase, this is usually dispersed in the dispersed phase which is dispersed in the outer phase. An emulsifying agent may or may not also be present.

The different types of emulsions may be defined by reference to the type of liquid forming the outer phase vs. the type of liquid forming the dispersed phase. In this connection, when an oil phase is dispersed in a water phase, the emulsion is terms "oi-in-water emulsion" or the "normal emulsion". However, it is also possible to form an "inverse or water-in-oil (w/o) emulsion". In an inverse emulsion, the water droplets are dispersed in a continuous phase of oil. It is to note that the term "emulsion" is also used herein to encompass multiple e.g., double, o/w/o, w/o/w emulsions. Once the oil in water emulsion is formed and the gel forming polymer is added, the solvent (or mixture of solvents) and the water are essentially removed.

Figure 2:
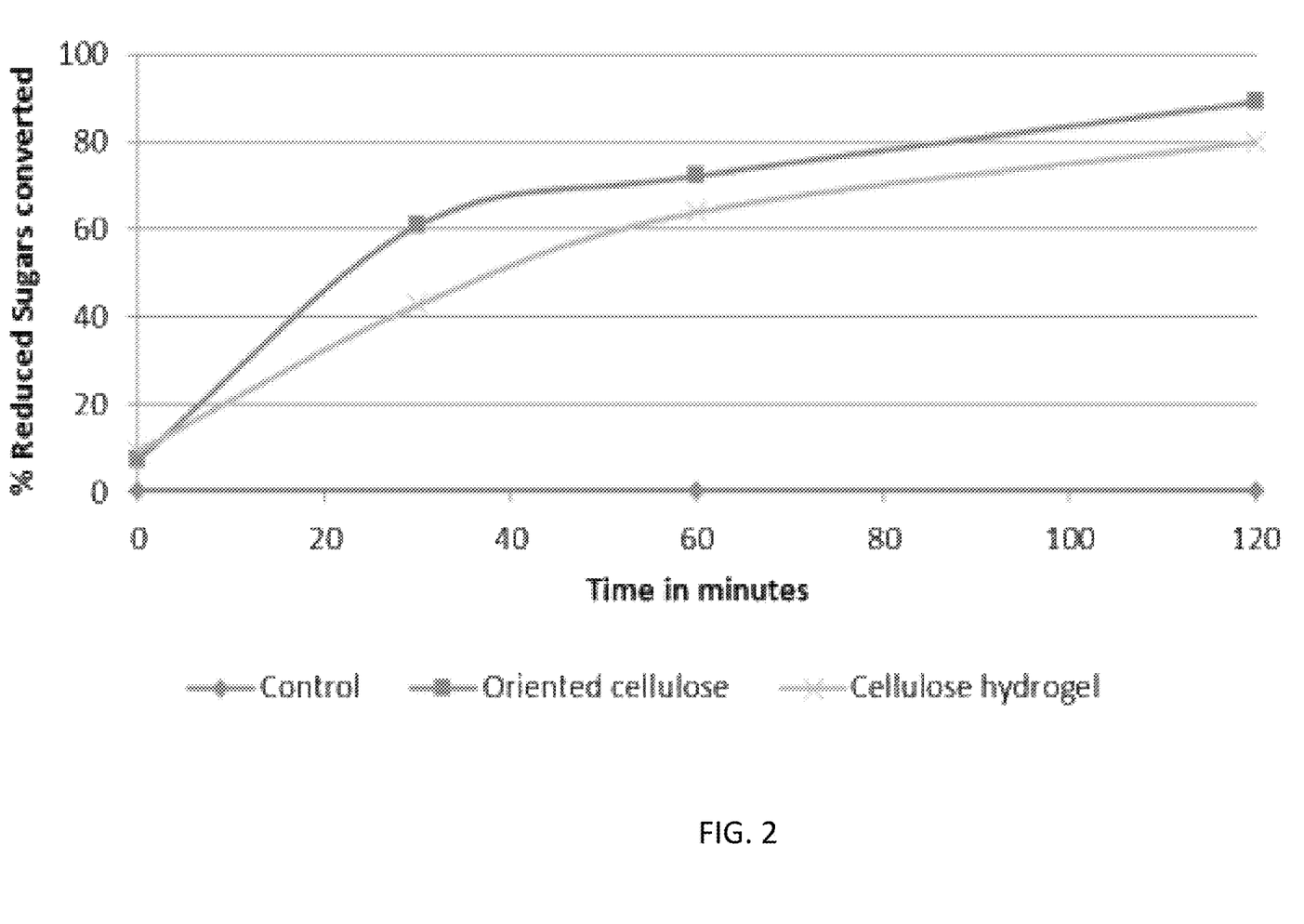
FIG. 2 presents graphs showing the enzymatic effect on the hydrolysis time for oil/cellulose emulsion vs. cellulose hydrogel.

As further shown in the Examples section below, the dispersion and emulsification are essential to increase surface and alter cellulose orientation. FIG. 2 shows that the enzymatic effect is improved (increased) when the cellulose is in the form of dispersed hydrogel and/or when the cellulose has specific intermolecular order (e.g., cellulose emulsified with oil and/or cellulose in the form of particle shells as disclosed herein).

As further shown in the Examples section below (FIG. 3) the enzymatic depolymerization effect is improved (increased) when the cellulose in hydrogel dispersion or oil emulsion is partially acetylated.

When forming capsules, initially water in oil emulsion may be formed and this w/o emulsion is converted to an o/w emulsion by the addition of water to the oil/organic phase.

Without being bound by a particular mechanism, it is assumed that the increase of cellulose molecules reactivity is derived from of their well-defined configuration at the oil/water interface thereby, inter alia, allowing the immediate use of the cellulose hydrolysis and fermentation sub-products in the processing of biodiesel.

Without being bound by any particular theory, it is assumed that natural cellulose molecules arrange in some ordered state onto boundary of oil and water. Self-ordered cellulose molecules in boundary of oil and water play role as surfactants stabilizing oil/water emulsion.

In some embodiments, spontaneously ordered molecules are in an amorphous state. Taken together, the ability of cellulose molecules to be in a well-defined configuration at the oil/water interface increases their reactivity.

In some embodiments, cellulose particles (e.g., capsules and/or in form of hydrogel and/or particles) of the invention are suspended in an aqueous liquid and used as an efficient medium for the enzymatic hydrolysis of cellulose to glucose. In some embodiments, provided herein is a method for high-efficiency hydrolysis of cellulose to saccharide compound (e.g., glucose).

By "high-efficiency hydrolysis" it is meant to refer to accelerating the rate of enzymatic hydrolysis by e.g., at least 1, 2, 3, 4, 5, 10, 15, 20, 25, 35, 40, 45, 50, 55, 60, 65, 65, 70, 75, 80, 85, 90, 95, 100, or 150 times, compared to the use of cellulose not in form of ordered state of cellulose molecules.

In some embodiments, by "high-efficiency hydrolysis" it is meant to refer to accelerating the rate of enzymatic hydrolysis by e.g., at least 1, 2, 3, 4, 5, 10, 15, 20, 25, 35, 40, 45, 50, 55, 60, 65, 65, 70, 75, 80, 85, 90, 95, 100, or 150 times, at a fixed quantity of enzymes compared to the use of cellulose not in form of ordered state of cellulose molecules.

In some embodiments, by "high-efficiency hydrolysis" it is meant to refer to reducing quantity of enzymes at a fixed rate of enzymatic hydrolysis compared to the use of cellulose not in form of ordered state of cellulose molecules.

In some embodiments, there is provided herein a method for high-efficiency production of bio-fuel (e.g., ethanol) by subsequent fermentation. In some embodiments, the bio-fuel is allowed to react with the oil medium, thereby forming biodiesel. In some embodiments, there is provided herein a method for increasing cellulose enzymatic accessibility. In some embodiments, there is provided herein a method for overcoming cellulose hydrolysis recalcitrance.

In some embodiments, cellulose hydrogel capsules of the invention suspended in an aqueous media, and comprising a cellulose hydrolyzing enzyme, provide enhancement of cellulose hydrolysis into e.g., glucose. In some embodiments, this efficiency is achieved due to at least one factor from the following five factors: (i) exceptionally high hydration of the cellulose hydrogel shell (e.g., liquid/cellulose weight ratio up to 99:1), (ii) full absence of crystallinity in cellulose hydrogel shell, (iii) exceedingly small cellulose shell thickness (e.g., less than 500 nm), (iv) high cellulose hydrogel porosity (about 3 cm/g) and (v) very high cellulose hydrogel shell specific surface area (e.g., more than 600 $m^2/g$).

In some embodiments, hydrolyzing enzyme is selected from, without being limited thereto, α-amylase, β-amylase, β-glucosidase, endo-cellulase, exo-cellulase, isoamylase, glucoamylase, pullulanase, cyclodextrin glucano-transferase, β-fructofuranosidase, glucose isomerase, glycoside hydrolase and combinations thereof.

In some embodiments, adsorbing particles on the borders of droplets is not reversible. Without being bound by any particular theory, the difference in the behavior of particles and surfactants is due to the fact that molecules of surfactants have a separated in space hydrophilic and hydrophobic parts, whereas the solid (e.g., Pickering) particles have an isotropic surface. Therefore, small solid particles cannot be packed in structures like micelles and they cannot be amphiphilic. A disadvantage of Pickering emulsions is that they are susceptible to Ostwald ripening, whereby diffusion through the continuous phase and between the droplets of the disperse phase (because of gaps between Pickering particles) can lead to an increase in the median droplet diameter over time or evaporation of the droplet content. This increase in droplet diameter increases the rate of separation of the disperse phase driven by density differences—either sedimentation or cream formation due to buoyancy. Ultimately, this ripening can render the product unfit for use because, for example, it requires re-homogenization, or because the droplets are too coarse to remain dispersed in the spray tank prior to application to the target, or because the droplets are too large to give even distribution of the active ingredient when applied to the target.

In some embodiments, non-derivatized microcrystalline or microfibrillar crystal cellulose powder, being partially wetted by both aqueous and oil phases, may adsorb at aqueous-oil interfaces and is capable of stabilizing emulsions (Pickering effect). A densely packed monolayer of cellulose particles or a three-dimensional network of particles of the present invention provides unexpected stability of these emulsions.

The cellulose particles remain at all time, in some embodiments, in an initial microcrystal or fibrillar crystal form (before and after formation of dispersions). This particles form interrupted mechanical scaffolding barrier around dispersed material, which does not hermetically covers of the droplets. In some embodiments, this hermetic molecular cellulose shell hinders the growth of the median droplet diameter over time and/or evaporation of the volatile droplet content.

In some embodiments, the compositions comprise a covering material that comprises or consists a non-particulate and non-crystal material-the cellulose of the invention. In some embodiments, the compositions are characterized by enveloping of droplets by continuous non-derivatized cellulose molecular layer(s) (at least one layer) or cellulose molecular network, which hermetically covers of the droplets.

In some embodiments, cellulose hydrogel capsules comprising a cellulose hydrolysis enzyme are provided in a phase-change material (PCM) as the oil embedded in the capsule. In some embodiments, the PCM system further promotes a beneficial spatial arrangement of the cellulose molecular planes in the hydrogel shell that further enhance the hydrolyzing enzymatic activity.

In some embodiments, the disclosed emulsion further comprises hydrolyzing enzyme. Non-limiting examples of hydrolyzing enzyme are selected from α-amylase, β-amylase, isoamylase, glucoamylase, pullulanase, cyclodextrin glucano-transferase, β-fructofuranosidase, glucose isomerase, glycoside hydrolase, and any combination thereof.

In some embodiments, the phase change of the PCM oil within the cellulose coated capsules from liquid to crystalline phase, in the cooling stage of the dispersion process, provides an added beneficial effect: the process of crystallization is accompanied by a reduction of the PCM core volume, thus the gap, formed between the cellulose hydrogel shell and the crystalline PCM core, is filled by the surrounding liquid with the enzyme that penetrates into the particle gap through the porous shell. In some embodiments, the phase change of the PCM oil within the cellulose coated capsules allows additional increase of the enzymatic hydrolysis caused by the optimal orientation of cellulose molecules turned to the internal side of the PCM particle shell. In some embodiments, the phase change temperature range of the PCM core material is specifically adjusted for optimum hydrolysis process.

In some embodiments, the process further comprises a step of fermenting the saccharide compounds, thereby forming at least one alcoholic compound, (i.e. forming a biofuel).

By "fermentation" it is meant to refer to a chemical change induced in a saccharide substance by the action of an enzyme, whereby the substance is split into simpler compounds. Specifically, the term "fermentation" includes the anaerobic dissimilation of substrates with the production of energy and reduced compounds, the final products thereof are organic acids, alcohols, such as, without being limited thereto, methanol, ethanol, isopropanol, butanol, etc., and $CO_2$. Such products, are typically secreted and are fermentation resultant of either microbial or yeast fermentation.

In some embodiments, step of fermenting the saccharide compounds generating a biofuel comprises culturing the microorganism under conditions that allow for biofuel formation, thereby generating the biofuel.

In some embodiments, the biofuel is selected from the group consisting of an alcohol, an alkene, and an alkane.

In some embodiments, the biofuel is selected from the group consisting of methanol, ethanol, propanol, isobutanol and n-butanol, or a combination thereof.

In some embodiments, the biofuel is derived from the cellulosic material. In some embodiments, the biofuel is derived from the starch. In some embodiments, the biofuel is produced from the cellulosic material and from the starch. In some embodiments, the biofuel is produced from the cellulosic material and from the starch simultaneously. In some embodiments, the biofuel is produced from the cellulosic material and from the starch separately. In some embodiments, the hydrolysis of cellulosic material and of the starch is performed separately. In some embodiments, the hydrolysis of cellulosic material and of the starch is performed simultaneously.

In some embodiments, the biofuel is recovered. Recovery of biofuels may be recovered according to methods known in the art. Alcohols such as ethanol, methanol, and/or butanol may be recovered from liquid material by molecular sieves, distillation, and/or other separation techniques. For example, ethanol can be concentrated by fractional distillation to about 90% or about 95% by weight. There are several methods available to further purify ethanol beyond the limits of distillation, and these include, but are not limited to, drying (e.g., with calcium oxide or rocksalt), the addition of small quantities of benzene or cyclohexane, molecular sieve, membrane, or by pressure reduction.

Other ways of collecting biofuel products include e.g., centrifugation, temperature fractionalization, chromatographic methods and electrophoretic methods.

In some embodiments, the alcoholic compound is extracted into oily phase. In some embodiments, the alcoholic compound is extracted by assistance of vacuum.

The purified biofuels products may be stoked in a separate container(s).

In some embodiments, solvent is at least partially removed from the emulsion.

There are several techniques available for removing a solvent (or solvent combination) from an emulsion, as known to those versed in the art including heating and solvent evaporation, volatile solvent evaporation followed by lyophilization etc. In some embodiments, the solvent is removed by spray drying, provided the active agents are not heat sensitive. In case the active agents are heat sensitive, other methods for removing solvent from an emulsion may be used, as known and appreciated by those versed in the art.

In some embodiments, the process further comprises a step of allowing the alcoholic compound (biofuel) to react with the oil medium, thereby forming a biodiesel. In some embodiments, the term "biodiesel" refers to short-chain (e.g., below $C_5$), alkyl esters.

In some embodiments and aspects of the invention, the process, or a step thereof, is operated in a reactor, in a batch or in continuous modes.

In some embodiments, the alcoholic compound produced by the fermentation is allowed to react with the oil medium. By "allowed to react" it is meant to refer to forming biodiesel, e.g., methyl, ethyl, iso-propyl or butyl esters by transesterification/esterification of the oil with the corresponding alcoholic compound.

In some embodiments, the reaction of the alcoholic compound, with the oil medium is a transesterification step. In some embodiments, the reaction of the alcoholic compound, with the oil medium is a transesterification step assisted by a catalyst. Herein the term "catalyst" may refer to a chemical catalyst and/or an enzyme as described hereinbelow.

In some embodiments, the abovementioned steps of:
(i) emulsifying the composition (e.g., cellulose or a derivative thereof), or providing an emulsified composition);
(ii) hydrolyzing the emulsified composition, thereby forming a saccharide compound;
(iii) fermenting the saccharide compounds, thereby forming an biofuel; and
(iv) allowing the biofuel to react with the oil medium, thereby forming biodiesel, are performed sequentially.

In some embodiments, the abovementioned steps (i) to (iv) are performed sequentially.

In some embodiments, at least two of steps (i) to (iv) are performed in one-pot.

In some embodiments, the abovementioned steps (i) to (iii) are performed sequentially. In some embodiments, the abovementioned steps (i) and (ii) are performed simultaneously. In some embodiments, the abovementioned steps (ii) and (iii) are performed simultaneously. In some embodiments, the abovementioned steps (iii) and (iv) are performed simultaneously. In some embodiments, the abovementioned steps (i) to (iii) are performed simultaneously. In some embodiments, the abovementioned steps (ii) to (iv) are performed simultaneously.

The term "simultaneously" is further meant to refer to fact that the products of the corresponding step are being produced contemporaneously, i.e. happening in, or are associated with, the same period of time. For example, when the abovementioned steps (ii) to (iv) are performed simultaneously the biofuel and the biodiesel are produced contemporaneously.

In some embodiments, the term "one pot" is meant to refer to a synthesis (or to a process) being carried out in a single reaction vessel, typically, but not exclusively, without removing therefrom any intermediate products.

In some embodiments, at least two steps of steps (i) to (iv) are performed sequentially and at least two steps of steps (i) to (iv) are performed simultaneously. In some embodiments, the steps (i) to (iv) are performed sequentially. In some embodiments, the steps (i) and (ii) are performed simultaneously. In some embodiments, step (ii) and step (iii) are performed simultaneously. In some embodiments, step (i), step (ii) and step (iii) are performed simultaneously. In some embodiments, step (iii) and step (iv) are performed simultaneously. In some embodiments, step (ii), step (iii) and step (iv) are performed simultaneously. In some embodiments, at least two steps of the step (i), step (ii), step (iii) and step (iv) are performed simultaneously. In some embodiments, at least two steps of the steps (i) to (iv) are performed sequentially.

In some embodiments, the concentration of the alcohol (e.g., ethanol) produced in the step of fermentation is maintained in the reaction medium at a concentration that varies within ±30%.

In some embodiments, the productions of the biofuel and biodiesel are processed simultaneously. In some embodiments, the productions of the biofuel and biodiesel are processed continuously.

In some embodiments, at least two of steps (i) to (iv) may be performed simultaneously, in one pot. In some embodiments, at least two of steps (i) to (iv) may be performed sequentially, in one pot, where step (iv) follows step (iii), step (iv) follows step (iii), step (iii) follows step (ii), and/or step (ii) follows step (i). Each possibility represents a separate embodiment of the present invention. In some embodiments, steps (i) to (iv) are performed in any sequence sequentially or simultaneously.

In some embodiments, the alcohol (e.g., ethanol) produced by any embodiments of the disclosed process ethanol is maintained at a defined concentration of about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15% (v/v), including any value therebetween.

In some embodiments, maintaining a defined alcoholic compound concentration in the medium is performed by controlled adsorption of the alcoholic compound into the oil medium. As described hereinabove the oil medium forms the core of the emulsion droplets.

In some embodiments, controlling the adsorption of the alcoholic compound into the oil medium is assisted by a phase separator tank. Further details of controlling the adsorption of the alcoholic compound into the oil medium are described below in the Examples section.

According to some embodiments of the invention ethanol is maintained at 5% concentration level.

Without being bound by any particular theory, it is believed that the products of each step of the process described herein (e.g., saccharide compounds, biofuel, and biodiesel) in the system is deposited at the oil water interface entrapping all the internal oil droplets and isolating them from the continuous aqueous phase.

As known in the art, biodiesel can be fabricated using e.g., bioethanol+oil+catalyst (e.g. enzymes).

In some embodiments, the catalyst is a chemical catalyst.

In some embodiments, the catalyst is selected from the group consisting of alkali-catalyst (for example, and without limitation, NaOH, KOH) or a combination thereof.

In some embodiments, the catalyst is an enzyme.

Non-limiting examples of enzymes are esterase e.g., lipases (e.g. *Ryzopus oryzae, Rhizomucor miehei, Mucor miehei, Pseudomonas fluorescens, Mucor javanicus, Candida rugosa* and *Rhizopus niveus,* as well as lipase OF from *Candida cylindracea* (*C. rugosa*) and lipase QLC (from *Alcaligenes* sp.) or a combination of them.

In some embodiments, oil/water volume ratio may be set, for example, to 1:6, 1:5, 1:4, 1:3, 1:2, 1:1, 2:1, 3:1, 4:1, 5:1, or 6:1, respectively, including any value therebetween.

In some embodiments, oil/ethanol volume ratio may be set to 1:6, 1:5, 1:4, 1:3, 1:2, 1:1, 2:1, 3:1, 4:1, 5:1, or 6:1, respectively, including any value therebetween.

In some embodiments, the step of producing biodiesel is carried out in water/oil environment, and alcohol (e.g., ethanol) is added to reaction. In some embodiments, the alcohol (e.g., ethanol) produced in step (iii) is dissolved in oil drops of the emulsion.

In some embodiments, the step of producing biodiesel is carried out in one-pot reaction, wherein the ethanol produced at fermentation in water environment can be self-diffused into oil drops of oil/water emulsion. Without being bound by any particular theory, it is assumed that self-diffusion is derived from better ethanol/oil solubility (interaction) vs. ethanol/water one. Transesterification reaction may occur within oil drops (i.e. in internal oil/water boundary of oil drops) with assistance of lipase enzymes inserted into oil drops. Lipase enzymes are located onto boundary of oil/water.

In some embodiments, the step of producing biodiesel is carried out such that a quantity of ethanol produced at fermentation are diffused into oil drops following conversion to e.g., ethyl esters (e.g., ethyl bio-diesel) by transesterification reaction.

In some embodiments, alcohol, e.g., methanol or ethanol produced at fermentation is extracted.

In some embodiments, a part of the alcohol is used for transesterification reaction and a part of the alcohol is extracted.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1

Dissolution and Regeneration

Exemplary process comprises of five steps: Cellulose containing raw material dissolution, hydrogel formation (coagulation), emulsification, hydrolysis and fermentation and product recovery.

The dissolution and regeneration of the cellulose containing raw material is important in altering cellulose crystallinity and surface. For dissolution each solvent has a unique procedure:

In exemplary procedures, cellulose containing raw material was introduced to the feed tank through the hopper and blended at constant RPM with the solvent at room temperature. The mixture was thereafter pumped out through a heat exchanger so as to reduce the solution temperature to −12° C. The mixture was kept for 2 minutes at that temperature to dissolve the cellulose.

In additional exemplary procedures, cellulose in ionic liquid (EMIMAc-1-ethyl-3-methylimidazolium acetate) was dissolved at 70° C. and 150 RPM until no crystalline cellulose is observed (5-20 min).

In additional exemplary procedures, cellulose in phosphoric acid was dissolved at room temperature or at 4° C. until no crystalline cellulose is observed (i.e. 5 min to 5 hours, depending on the cellulose concentration).

Hydrogel formation: In exemplary procedures, the cellulose solution coagulated by adding water (from filtrate vessel) so as to remove urea and NaOH. Two rotary vacuum drum filters were used for solvent recovery and reducing fresh water usage. The first filtrate for solvent recovery was richer in urea NaOH and the second filtrate used for first coagulation was leaner in urea NaOH. During the two filtration systems, the hydrogel formed on the retentate side and at the end directed to the premix tank.

Example 2

Dispersion and Emulsification

The dispersion and emulsification are aimed at increasing the surface area and alter the cellulose intermolecular order. Several types of homogenizers can be used for this process, high shear homogenizer and high pressure homogenizer.

In exemplary procedures, dispersion and emulsion processing were assisted by several homogenizers: mechanical homogenizer—enabling homogenization by high shear forces created by 3000-25000 RPM rotating discs; and ultrasonic homogenizer—at frequency of 20 kHz, and high-pressure homogenizer with working pressure up to 200 MPa.

Emulsification: hydrogel at the premix tank was mixed with certain amount of oil to perform a premix (oil, water and hydrogel). The premix was pumped to the homogenizer to form emulsion particles.

Example 3

Enzymatic Digestion and Fermentation

In exemplary procedures, enzymatic saccharification of emulsified cellulose was conducted at 50° C. for separate hydrolysis and fermentation (SHF), 34-37° C. for simultaneous saccharification and fermentation (SSF) and 150 rpm in a 50 mM sodium acetate buffer (pH of 4.8). Accellerase1500® (Du Pont), Celluclast® 1.5 (Novozymes) and Cellobiohydrolase® were used for enzymatic saccharification.

In exemplary procedures, for fermentation, dry yeast was used, for example Thermosacc® DRY (Lallemand Biofuels & Distilled Spirits Ltd.), at optimal temperature of 34-37° C. and pH 4.8.

In exemplary procedures, emulsion particles were introduced to jacketed controlled environment tank reactor with constant stirring speed and temperature that was calibrated for SHF (at 50° C.) or SSF (at 37° C.). In the reactor a certain amount of enzymes and fermenters was used to convert cellulose emulsion to glucose and bioethanol. Choosing yeast as the fermenters allowed processing in an anaerobic condition.

FIG. 1 presents graphs showing the enzymatic effect on the particle sizes and on glucose formation for cellulose hydrogel vs. microcrystalline cellulose.

FIG. 2 presents graphs showing the enzymatic effect on the hydrolysis time for oil/cellulose emulsion vs. cellulose hydrogel dispersion.

In additional exemplary procedures, acetylated cellulose is used.

Table 1 below presents the effect of slight cellulose acetylation on the level of cellulose enzymatic hydrolysis conversion of the slightly acetylated cellulose hydrogel dispersion and oil emulsion, coated by slightly acetylated cellulose:

TABLE 1

| Time, min | Slightly acetylated cellulose hydrogel, % | Micro-crystalline cellulose, % | Cellulose hydrogel dispersion, % | Emulsion of oil, coated by slightly acetylated cellulose hydrogel, % |
|---|---|---|---|---|
| 0 | 0.0 | 0.0 | 0.0 | 0.00 |
| 1 | 53.1 | 0.0 | 0.0 | 65.3 |
| 15 | 77.2 | 0.0 | 12.0 | 68.2 |
| 30 | 79.5 | 0.3 | 26.8 | 84.5 |
| 60 | 80.5 | 3.1 | 45.1 | 88.4 |

Figure 3:
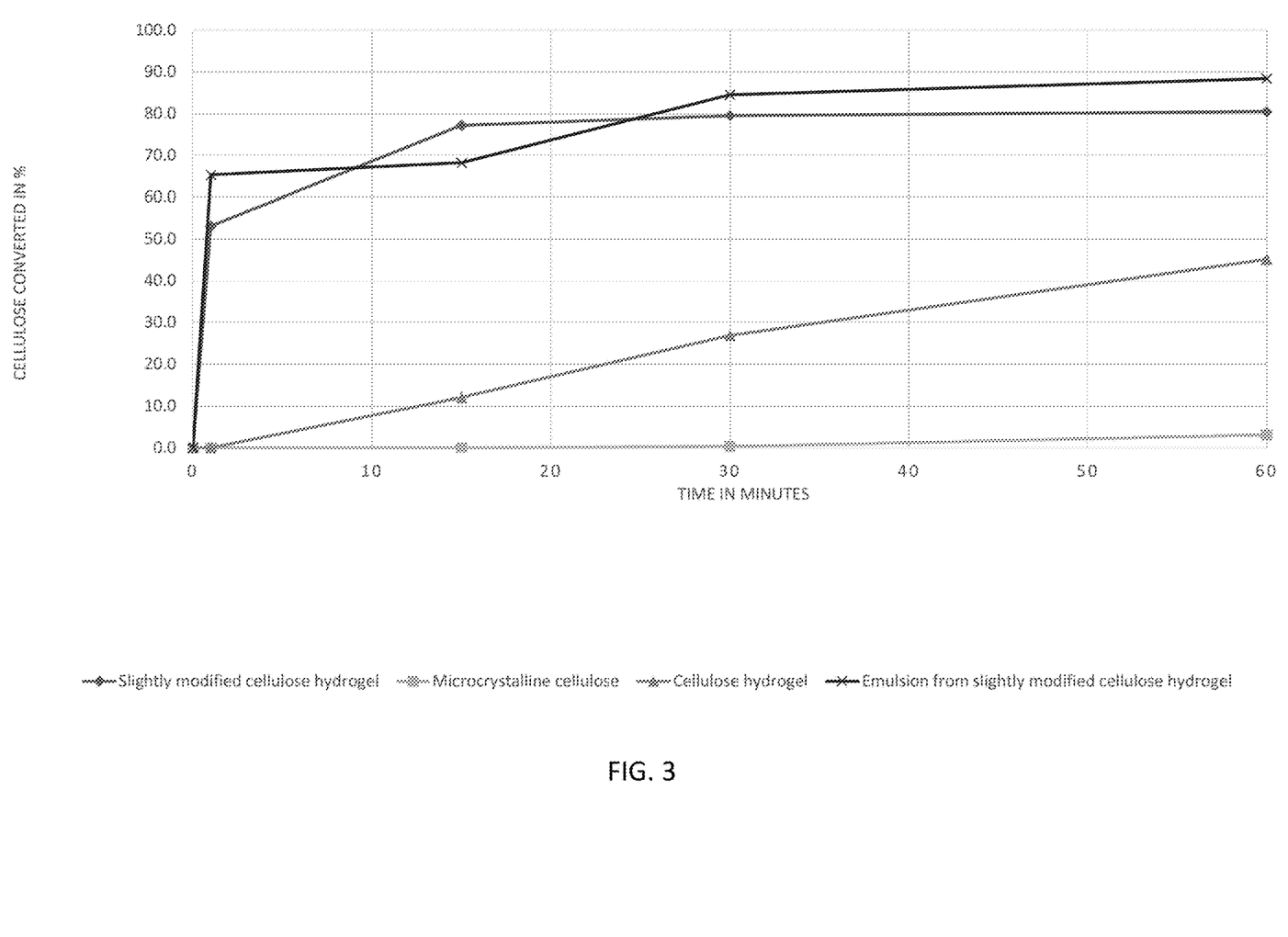
FIG. 3 presents graphs showing the effect of cellulose acetylation on the level of cellulose enzymatic hydrolysis conversion of the hydrogel and emulsion.

The results are further visualized in FIG. 3.

Without being bound by any particular mechanism, it is assumed that the biodegradability of cellulose ester derivatives (using a degradation assay based on commercially available cellulolytic enzyme preparations) depends on 3 factors: degree of substitution, substituent size and cellulose derivative morphology. The smaller the substituent, the higher the degree of substitution that can be tolerated by cellulolytic enzymes. Thus, the higher and the more homogeneous the degree of molar substitution of the polysaccharide derivative, the greater should its resistance be to enzyme depolymerization.

Herein, as demonstrated e.g., in FIG. 3, it was found that the enzymatic hydrolysis of cellulose derivatives (in partial, e.g., cellulose esters, such as secondary cellulose acetates) in the form of hydrogel dispersion or cellulose coated oil emulsion by the standard enzymes is hundreds of times faster than in all known conventional processes. The effect is observed in case of cellulose acetates with a degree of substitution in the range of 0.4-1.3 (that equivalent to the acetyl content of 11-30 wt. %).

Example 4

Product Recovery

Since the accumulation of glucose and/or alcohols in the reaction medium might inhibit the hydrolysis and fermentation processes, maintaining of these materials in the reaction mixture at the optimal level was carried out by the controlled evacuation of the extent of aqueous glucose solution and simultaneous vacuum evaporation and oil adsorption of alcohols.

The control of hydrolysis and fermentation processes and product recovery depend on reactor usage. In case of separate hydrolysis and fermentation, the lower stream of the reactor was directed to a phase separator unit, and in this unit, the oil phase was collected for reuse and water phase recycled to the reactor with a side stream for glucose fermentation. In case of simultaneous saccharification and fermentation, the lower stream of the reactor was directed to a phase separator tank, with the stream comprising mainly water oil and ethanol. The water phase with certain amount of ethanol was recycled to the reactor and the oil phase with certain amount of ethanol was pumped into distillation tank for ethanol recovery. The product and the oil were recycled for reuse.

In additional exemplary procedures, this process was adjusted for using ionic liquid or phosphoric acid as solvent instead of urea/NaOH by a single change, and the heat exchanger for cooling the solution was replaced by jacketed stirred feed tank.

Example 5

Examples of Processing Bio-Ethanol and Bio-Butanol

Bio-ethanol: Thermosacc® Dry yeast by Lallemand Biofuels & Distilled Spirits was used (as model example of yeast) to ferment saccharides produced by innovative method. The temperature of processing was about 34° C. The concentration of ethanol in zone of reaction was kept on level of about 2% so as to avoid damping of the ethanol.

The reaction of fermentation was carried out sequentially with production of saccharides as well as simultaneously in one pot.

In exemplary procedures (referred to as: "simultaneous schema"), the saccharides produced was fermented simultaneously to ethanol. In this case the reaction of hydrolysis of cellulose (production of saccharides) and following fermentation of saccharides is performed in one place.

In additional exemplary procedures (referred to as: "sequential schema"), saccharides are produced at one place and time and fermented at another place and time.

In additional exemplary procedures (referred to as: "hybrid schema"), combining simultaneous and sequential schema is applied when part of saccharides is fermented to ethanol simultaneously and part at another place and time.

The maximum optimal speed of reactions is determined by enhanced speed of hydrolysis reactions.

In additional exemplary procedures, the enhanced hydrolysis reactions is carried out both at enhanced speed of reactions or at reduced quantity of the necessary enzymes.

Bio-butanol: as known in the art, the fabrication of bio-butanol from saccharides may be produced using either bacterium *Clostridium acetobutylicum* or *Ralstonia eutropha* H16, or other suitable fermentation mediums. As known in the art, the difference from ethanol production is primarily in the fermentation of the feedstock and minor changes in distillation.

As known in the art, non-effective fermentation (a low yield of butanol per gram of glucose) is the major reason for unsuccessful current state of production of bio-butanol.

According to DuPont, existing bioethanol plants can cost-effectively be retrofitted to bio-butanol production.

In exemplary procedures, carrying the reaction of fermentation (butanol production) is conducted sequentially with production of saccharides as well as simultaneously at one pot and by the hybrid schema. The production of butanol can be enhanced by enhanced speed of the hydrolysis of the cellulose (production of saccharides).

Example 6

Examples of Processing Biodiesel

Production of bio-diesel using NaOH as a model catalyzer: Vegetable oil was transesterified forming ethanol at a medium having ratio of about 100 ml of oil to 50 ml of ethanol and 0.5 g sodium hydroxide (NaOH) at a temperature of about 60° C. and atmospheric pressure. After the transesterification reaction, the content of ethyl esters (bio-diesel) reached at least 96% for optimal product performance. Ethanol was taken with excess so as to complete transesterification reaction. Ethyl esters were next removed from ethanol and were thereafter cleaned from soap by centrifugation, fresh water circulation, purification step, and by using sorbents.

At the final stage, fatty acid ethyl esters were dried from water. A by-product of the to transesterification process was the production of glycerin. For 10 gram of biodiesel, about 1 gram of glycerin, that may be used separately, was produced.

The yield of biodiesel production was increased with the increase of ethanol/oil ratio and with the amount of sodium hydroxide catalyst. At least 1 hour of reaction time is necessary to reach an optimal highest yield of biodiesel.

Production of bio-diesel using enzymes as catalyzers: As known in the art, biodiesel can be fabricated using e.g., bioethanol+oil+enzymes as catalyzers. Vegetable, animal or algae oils can be used. Enzymes can be used are lipase kinds such as lipase from *Rhizomucor miehei*, lipase from *Mucor miehei*, lipase from *Pseudomonas fluorescens*, lipase from *Mucor javanicus*, lipase from *Candida rugosa* and *Rhizopus niveus* can be used as well as lipase OF from *Candida cylindracea* (*C. rugosa*) and lipase QLC (from *Alcaligenes* sp.) or a combination of them.

In exemplary procedures, oil/water volume ratio was set for example, as 6:1 and oil/ethanol volume ratio was set as the same ratio. The reaction was carried out in water/oil environment and, in exemplary procedures, ethanol was added to the reaction vessel.

At simultaneous schema (one-pot) ethanol produced at fermentation in water environment is self-diffused into oil drops of oil/water emulsion. Self-diffusion is derived from better ethanol/oil solubility (interaction) vs. ethanol/water one.

Transesterification reaction occurs within oil drops (i.e. in internal oil/water boundary of oil drops) with assistance of lipase enzymes inserted into oil drops. Lipase enzymes are located onto boundary of oil/water.

In exemplary procedures simultaneous schema, a quantity of ethanol produced at fermentation were diffused into oil drops with following conversion to ethyl esters (ethyl bio-diesel) by transesterification reaction.

In exemplary sequential schema, ethanol produced at fermentation was extracted.

Ethanol was then added for conducting the transesterification reaction for production of bio-diesel in another place and time. In exemplary sequential schema, methanol was used for production of bio-diesel as well.

In exemplary procedures, hybrid schema was applied when partly ethanol can be used for transesterification reaction and partly extracted.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A process for the preparation of biodiesel, the process comprising the steps of:
   (a) providing a composition comprising an interior medium encapsulated by at least one layer facing an exterior medium, wherein said interior medium comprises a hydrophobic medium and said exterior medium comprises a hydrophilic medium, or said interior medium comprises a hydrophilic medium and said exterior medium comprises a hydrophobic medium; and wherein said at least one layer comprises at least one of cellulose, a cellulose derivative material, and starch;
   (b) contracting said composition with a cellulose hydrolyzing enzyme, thereby hydrolyzing said at least one layer to form saccharide compounds,
   (c) fermenting said saccharide compounds by contacting said saccharide compounds with a fermenting microorganism, thereby forming at least one alcoholic compound; and
   (d) reacting said at least one alcoholic compound with said hydrophobic medium under presence of a catalyst, thereby forming a biodiesel, wherein
   steps (b) to (d) are performed simultaneously in one-pot at a temperature compatible with said fermenting microorganism.

2. The process of claim 1, wherein said composition comprises at least one layer of secondary cellulose acetate.

3. The process of claim 1, wherein said composition is dispersed and/or emulsified.

4. The process of claim 1, wherein said cellulose, said cellulose derivative material, and/or said starch is nano-sized.

5. The process of claim 1, wherein said cellulose, said cellulose derivative material, and/or said starch is micro-sized.

6. The process of claim 1, wherein said cellulose, said cellulose derivative material, and/or said starch is in the form selected from the group consisting of hydrogel, amorphized structure, crystalline structure, and mixture thereof.

7. The process of claim 1, wherein said alcoholic compound is selected from methanol and ethanol.

8. The process of claim 1, wherein said at least one layer is in a form selected from one or more continuous molecular layers, one or more groups of separated particles, and any mixture thereof.

9. The process of claim 1, wherein said at least one alcoholic compound is maintained at a concentration ranging from 0.1% to 10% (v/v.), optionally, wherein said concentration varies within ±30%.

10. The process of claim 1, wherein the composition is selected from oil-in-water (o/w) emulsion, water-in-oil (w/o) emulsion and any combination thereof, optionally, wherein the composition is devoid of a surfactant.

11. The process of claim 1, wherein said hydrophobic medium is an oil comprising one or more compounds selected from the group consisting of: natural vegetable, algae or organic oils (lipids), polyglycol, an alkane, an alkene, an alkyne, an aromatic hydrocarbon, or any combination thereof.

12. The process of claim 1, wherein said composition is in the form of a capsule comprising a shell and a core, optionally wherein said capsule is 10 nm to 1000 μm in diameter, and optionally wherein a thickness of said shell thickness ranges from about 0.1% to about 500% of the core.

13. The process of claim 1, wherein said cellulosic material is an emulsifying agent.

14. The process of claim 1, wherein said cellulose hydrolyzing enzyme is selected from the group consisting of α-amylase, β-amylase, isoamylase, glucoamylase, pullulanase, cyclodextrin glucano-transferase, α-fructofuranosidase, glucose isomerase, glycoside hydrolase and combinations thereof.

15. The process of claim 1, wherein said biodiesel is a product of a transesterification reaction of said alcoholic compound with said hydrophobic medium, wherein the transesterification reaction is assisted by said catalyst, wherein said catalyst is selected from the group consisting of alkali-catalyst, or is an enzyme selected from one or more lipases.

16. The process of claim 15, wherein said one or more lipases are selected from *Ryzopus oryzae, Rhizomucor miehei, Mucor miehei, Pseudomonas fluorescens, Mucor javanicus, Candida rugosa* and *Rhizopus niveus*, as well as lipase OF from *Candida cylindracea* (*C.rugosa*) and lipase QLC from *Alcaligenes* sp. and a combination thereof.

17. The process of claim 1, wherein said fermenting microorganism comprises at least one of yeast and a bacterium.

18. The process of claim 12, wherein said capsule is a micro-sized capsule.

* * * * *